United States Patent
Morita (10) Patent No.: US 9,188,686 B2
(45) Date of Patent: Nov. 17, 2015

(54) RADIATION DETECTOR ASSEMBLY AND SAMPLE ANALYZER

(71) Applicant: JEOL Ltd., Tokyo (JP)

(72) Inventor: Masaki Morita, Tokyo (JP)

(73) Assignee: JEOL Ltd., Tokyo (JP)

( * ) Notice: Subject to any disclaimer, the term of this patent is extended or adjusted under 35 U.S.C. 154(b) by 344 days.

(21) Appl. No.: 14/179,977

(22) Filed: Feb. 13, 2014

(65) Prior Publication Data
US 2015/0276952 A1 Oct. 1, 2015

(30) Foreign Application Priority Data
Mar. 6, 2013 (JP) .................................. 2013-043925

(51) Int. Cl.
*G01N 23/223* (2006.01)
*G01T 7/00* (2006.01)
*G01N 23/207* (2006.01)

(52) U.S. Cl.
CPC ............ *G01T 7/005* (2013.01); *G01N 23/2076* (2013.01); *G01N 23/223* (2013.01); *G01N 2223/076* (2013.01)

(58) Field of Classification Search
CPC .... G01T 1/026; G01T 7/005; G01N 23/2076; G01N 23/223; G01N 2223/076
See application file for complete search history.

(56) References Cited

FOREIGN PATENT DOCUMENTS

JP 1048161 A 2/1998

*Primary Examiner* — Mark R Gaworecki
(74) *Attorney, Agent, or Firm* — The Webb Law Firm (57) ABSTRACT

Disclosed is a radiation detector assembly which can easily make a decision as to whether an energy calibration is needed. The radiation detector assembly detects radiations, creates pulse signals having pulse heights corresponding to the energies of the radiations, converts the pulse heights of the pulse signals into energies, and creates a radiation spectrum. The radiation detector assembly includes a qualitative analysis portion for assigning peaks appearing in the radiation spectrum, a conversion value calculating portion for calculating energy conversion values for converting the pulse heights into the radiation energies based on the assigned peaks, and an energy calibration decision portion for making a decision as to whether an energy calibration is needed, based on the calculated energy conversion values.

7 Claims, 10 Drawing Sheets

RADIATION DETECTOR ASSEMBLY AND SAMPLE ANALYZER

CROSS-REFERENCE TO RELATED APPLICATION

This application claims priority to Japanese Patent Application No. 2013-043925 filed Mar. 6, 2013, the disclosure of which is hereby incorporated by reference in its entirety.

BACKGROUND OF THE INVENTION

1. Field of the Invention

The present invention relates to a radiation detector assembly and also to a sample analyzer.

2. Description of the Related Art

Radiation detector assemblies are apparatus for detecting radiations (such as X-rays and gamma rays (γ-rays)) and constructing radiation spectra. Known radiation detector assemblies of this type include energy-dispersive X-ray spectrometers (EDS) and wavelength-dispersive X-ray spectrometers (WDS).

In an energy-dispersive X-ray spectrometer, a distribution of pulse heights is created by a multichannel analyzer (MCA). Since this is a distribution of pulse heights at this moment, an X-ray spectrum is not yet completed. Accordingly, the pulse heights are converted into X-ray energies, thus producing an X-ray spectrum. Generally, the following formula (1) is used in converting pulse heights (ch) into X-ray energies (E):

$$E = \text{gain} \times ch + \text{offset} \quad (1)$$

In the energy-dispersive detector, an energy calibration is done, for example, by making a measurement on a reference sample containing a known element and used for energy calibration and by finding the gain and offset included in Eq. (1) above.

For example, in an X-ray fluorescent analyzer using an energy-dispersive detector, energy positions may deviate due to aging of the detector and signal processing circuitry in the stage following the detector. That is, positions taken along the horizontal axis of the X-ray fluorescent spectrum may deviate. If energy position deviations increase to some extent, and if a spectral line of a certain element is present, the difference between the energy corresponding to the spectral line and the theoretical energy corresponding to the element is increased. This creates the danger that the spectral line will not be identified as corresponding to the element or that the spectral line might be misidentified as corresponding to other element, i.e., an incorrect elemental assignment is made. Accordingly, in order to correct for deviation of energy position as described above, an energy calibration is done.

For example, JP-A-10-48161 discloses an X-ray fluorescent analyzer having a shutter to which a reference sample for energy calibration is directly attached. Thus, the reference sample is kept in the instrument. This eliminates the labor to exchange the reference sample. Hence, this analyzer permits an energy calibration to be done quickly and easily.

In the past, the analyzer himself or herself has made a decision as to whether an energy calibration routine as described above is needed. In particular, the use time and number of uses of the instrument are managed. It is determined that an energy calibration is needed whenever a given operating time has passed or a given number of uses are reached. Then, an energy calibration using a sample for energy calibration is carried out.

With this method, however, it is not always possible to appropriately determine whether the condition needs an energy calibration. Therefore, an energy calibration may be carried out in spite of the condition in which no calibration is necessary.

Furthermore, if the frequency of energy calibration operations is lowered in an attempt to avoid unwanted energy calibration operations, then there is the danger that the energy position deviation might exceed the tolerable range, for example, during continuous measurement on plural samples. In this case, it is not obvious when the energy position deviation exceeded the tolerable range. Consequently, all the results of measurements already obtained are discarded because they are regarded as unreliable. Alternatively, it may be necessary to perform a work for evaluating whether each individual measurement result is correct or not.

SUMMARY OF THE INVENTION

In view of the foregoing problem, the present invention has been made. According to some aspects of the present invention, it is possible to offer radiation detector assembly and sample analyzer permitting one to easily judge whether an energy calibration is needed.

(1) A radiation detector assembly associated with the present invention detects radiations, produces pulse signals having pulse heights corresponding to energies of the radiations, converts the pulse heights of the pulse signals into energies, and creates a radiation spectrum. The radiation detector assembly includes: a qualitative analysis portion for assigning peaks appearing in the radiation spectrum; a conversion value calculating portion for calculating energy conversion values used to convert the pulse heights into the radiation energies based on the assigned peaks; and an energy calibration decision portion for making a decision, based on the calculated energy conversion values, as to whether an energy calibration is needed.

According to this radiation detector assembly, the energy conversion values can be calculated based on peaks assigned by a qualitative analysis, and a decision can be made as to whether an energy calibration is needed. Consequently, even if any measurement on a reference sample for energy calibration is not performed, it is possible to judge whether an energy calibration is necessary from the results of measurements on a sample containing unknown elements. Hence, it is easy to make a decision as to whether an energy calibration is required.

(2) In one feature of this radiation detector assembly, there may be further provided a notification portion which gives a notice as to whether an energy calibration is needed based on the result of the decision made by the energy calibration decision portion.

(3) In another feature of this radiation detector assembly, there may be further provided an energy calibration portion which, if the energy calibration decision portion has determined that an energy calibration is needed, performs an energy calibration using the energy conversion values calculated by the conversion value calculating portion.

(4) In a further feature of this radiation detector assembly, there may be further provided a conversion value calculation decision portion for making a decision as to whether the energy conversion values should be calculated, based on the assigned peaks. If the conversion value calculation decision portion has determined that the energy conversion values are not calculated, the conversion value calculating portion may not need to calculate the energy conversion values.

(5) In an additional feature of this radiation detector assembly, the conversion value calculating portion may calculate the energy conversion values, based either on a reference spectrum for an element to which the assigned peaks correspond or on a base function.

(6) In a yet other feature of this radiation detector assembly, there may be further provided: a resolution calculating portion for calculating an energy resolution calibration value, based on the assigned peaks, to convert the pulse heights into the radiation energies; and a resolution calibration decision portion for making a decision as to whether energy resolution needs to be calibrated, based on the calculated energy resolution calibration value.

(7) A sample analyzer associated with the present invention includes a radiation detector assembly associated with the present invention.

According to this sample analyzer, energy conversion values are calculated based on the peaks assigned by a qualitative analysis, and it is possible to make a decision as to whether an energy calibration is needed. Consequently, if any measurement on a reference sample for energy calibration is not performed, it is possible to make a decision, based on the results of measurements on a sample containing unknown elements, as to whether an energy calibration is needed. Thus, it is easy to make a decision as to whether an energy calibration is necessary.

DETAILED DESCRIPTION OF THE INVENTION

The preferred embodiments of the present invention are hereinafter described in detail with reference to the drawings.

It is to be understood that the embodiments provided below do not unduly restrict the scope of the present invention delineated by the appended claims and that not all the configurations described below are essential constituent components of the invention.

1. Configuration of Sample Analyzer

Figure 1:
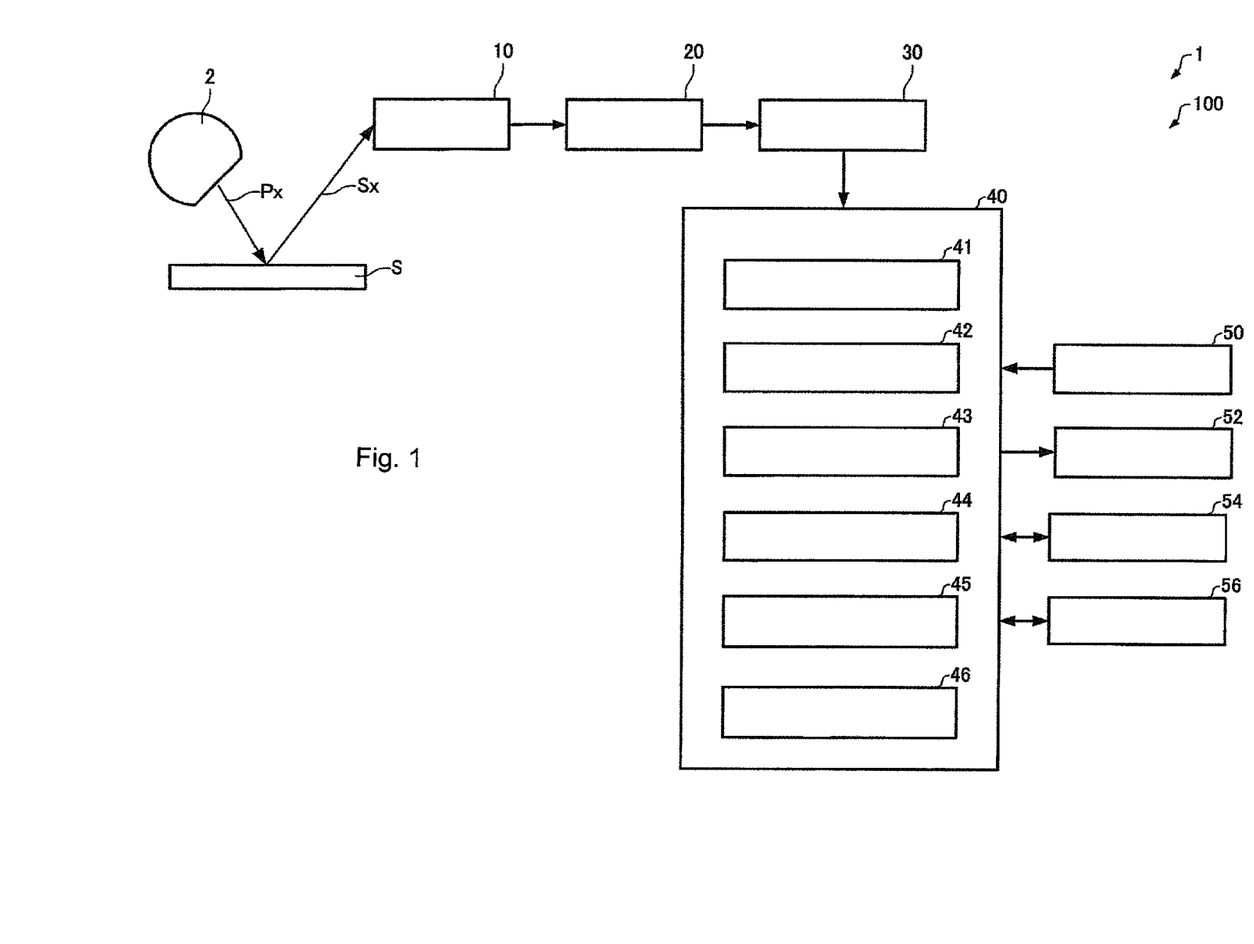
FIG. 1 is a block diagram of a sample analyzer associated with one embodiment of the present invention, showing the configuration of the analyzer.

First, the configuration of a sample analyzer associated with one embodiment of the present invention is described by referring to FIG. 1, where the analyzer is generally indicated by reference numeral 1.

The sample analyzer 1 is configured including a radiation detector assembly associated with the present invention. The radiation detector assembly is generally indicated by reference numeral 100.

The sample analyzer 1 is configured including an excitation source 2 and the radiation detector assembly 100.

In the sample analyzer 1, the excitation source 2 irradiates a sample S with primary X-rays, Px. Secondary X-rays (such as fluorescent X-rays or characteristic X-rays) Sx emitted from the sample S in response to the irradiation are detected by the radiation detector assembly 100. For example, the sample analyzer 1 is an energy-dispersive X-ray fluorescent spectrometer.

The excitation source 2 which irradiates the sample S with the primary X-rays Px is configured including an X-ray tube and a high-voltage source, for example. The excitation source 2 produces the primary X-rays Px by accelerating thermionic electrons constructed from a filament by a high voltage such that the electrons collide against a metal target in an unillustrated manner.

As shown in FIG. 1, the radiation detector assembly 100 is configured including a detector 10, a pulse processor 20, a multichannel analyzer 30, a spectrum analysis system 40, a manual control unit 50, a display unit 52, a storage portion 54, and a storage medium 56.

The detector 10, which detects the secondary X-ray Sx, is a semiconductor detector such as an Si (Li) detector having a single silicon crystal into which lithium has been diffused (known as drifting) or a silicon drift detector having Si to which a drift voltage is applied. The detector 10 is an energy-dispersive detector and provides an output of staircase waveform having steps whose heights correspond to the energies (wavelengths) of incident X-rays.

The pulse processor 20 converts the height of each step of the output signal of staircase waveform from the detector 10 into a corresponding number of pulses and produces pulse signals.

The multichannel analyzer 30 discriminates the incident pulses according to their pulse heights, counts the numbers of the pulses, and creates a graph of a pulse height distribution. In particular, the multichannel analyzer 30 first digitizes the output signal (analog pulse signal) from the pulse processor 20, obtains pulse height values of the resulting digital pulses, discriminates the individual pulses according to their peaks, counts the numbers of the pulses, and creates a graph of a distribution of pulse heights. The multichannel analyzer 30 creates the graph of the distribution of pulse heights (FIG. 3) by making the pulse heights of the pulse signals correspond to the channels of the multichannel analyzer 30 and creating the distribution of pulse heights from the numbers of pulses counted for each channel.

The manual control unit 50 permits a user to enter control information. The manual control unit 50 outputs the entered control information to the spectrum analysis system 40. The functions of the manual control unit 50 can be realized by a keyboard, computer mouse, touch panel display, or other hardware unit.

The display unit 52 operates to display an image constructed by the spectrum analysis system 40. The functions of the display unit 52 can be implemented by an LCD, CRT, or the like. The display unit 52 can display information indicating whether or not an energy calibration is needed, for example.

The storage portion 54 operates as a working region for the spectrum analysis system 40. The functions of the storage portion 54 can be accomplished by a RAM or the like. Programs and data are stored in the storage medium 56 that can be read by a computer. The functions of the storage medium 56 can be accomplished by an optical disc (such as a CD or DVD), a magnetooptical disc (MO), a magnetic disc, a hard disc, magnetic tape, or a memory (such as a ROM). The spectrum analysis system 40 performs various kinds of processing according to the present embodiment based on the program and data stored in the storage medium 56. Programs for causing a computer to operate as various portions of the spectrum analysis system 40 can be stored in the storage medium 56.

The spectrum analysis system 40 performs various processing operations such as an operation for constructing an X-ray spectrum, an operation for assigning peaks appearing in the X-ray spectrum (i.e., qualitative analysis), an operation for calculating energy conversion values for converting pulse heights into radiation energies, an operation for making a decision as to whether an energy calibration is needed, an operation for giving a notice as to whether an energy calibration is needed, and an operation for making a decision as to whether energy conversion values are calculated. The functions of the spectrum analysis system 40 can be realized by various processors (such as a CPU or DSP), an ASIC (such as a gate array), or other hardware unit or by software. The spectrum analysis system 40 is configured including a spectrum constructor 41, a qualitative analysis portion 42, a conversion value calculation decision portion 43, a conversion value calculating portion 44, an energy calibration decision portion 45, and a notification portion 46.

The spectrum constructor 41 constructs an X-ray spectrum (see FIG. 4) based on the pulse height distribution graph (see FIG. 3) created by the multichannel analyzer 30. In particular, the spectrum constructor 41 constructs the X-ray spectrum by converting each channel (pulse height value) ch plotted on the horizontal axis of the pulse height distribution graph into an energy E using the following energy conversion formula (1).

$$E = A \times ch + B \tag{1}$$

where A and B are energy conversion values. A is a gain. B is an offset. The gain A and offset B are coefficients in the energy conversion formula (1).

The energy conversion values A and B are obtained by performing energy calibration (i.e., to correct deviation of energy position (taken along the horizontal axis of the X-ray spectrum). Deviation of the energy position can be corrected by calculating appropriate energy conversion values A and B, and an energy calibration can be done.

The qualitative analysis portion 42 performs a qualitative analysis consisting of assigning peaks appearing in the X-ray spectrum. In the radiation detector assembly 100, information about the energy values of the characteristic X-rays possessed by elements is held as a database (characteristic X-ray database) in the storage portion 54. The qualitative analysis portion 42 performs elemental assignment of each peak of the X-ray spectrum, based on the characteristic X-ray database. The qualitative analysis portion 42 can perform a qualitative analysis using a well known method of quantitative analysis.

The conversion value calculation decision portion 43 makes a decision based on the assigned peaks as to whether the energy conversion values should be calculated. If the assigned peaks are not appropriate for calculation of the energy conversion values, the conversion value calculation decision portion 43 determines that the energy conversion values are not calculated.

In a method (described later) of calculating energy values by the conversion value calculating portion 44, if peaks are close to each other or overlap with each other, it is difficult to calculate the energy conversion values accurately. In order to accurately compute the energy conversion values, it is desired that the difference between the energy values of two peaks used for calculation of the energy conversion values be 1 keV or higher. Accordingly, if any assigned peaks in the X-ray spectrum do not produce peak-to-peak energy difference values equal to or greater than 1 keV, the conversion value calculation decision portion 43 determines that the energy conversion values are not calculated.

The decision criterion as to whether or not the energy conversion values are calculated is not restricted to the above-described criterion. For example, the decision may be made depending on whether the peak width of a peak of interest is greater than the energy resolution of the radiation detector assembly 100 that is assumed from the energy position of this peak. That is, if the peak width of the peak of interest is greater than the energy resolution of the radiation detector assembly 100, the conversion value calculation decision portion 43 regards the peak of interest as overlapping with other peak and may determine that the energy conversion values are not calculated.

The conversion value calculating portion 44 calculates the energy conversion values A and B (coefficient in energy conversion formula (1)) to convert pulse heights into X-ray energies based on the assigned peaks.

From the energy conversion formula (1), the gain A and offset B are expressed by the following formulas:

$$A = (E_\beta - E_\alpha)/(X_\beta - X_\alpha) \tag{2}$$

$$B = (E_\beta \times X_\alpha - E_\alpha \times X_\beta)/(X_\beta - X_\alpha) \tag{3}$$

where $\alpha$ is a chemical element, $X_\alpha$ is the energy value of an assigned peak, $\beta$ is another chemical element, $X_\beta$ is the energy value of an assigned peak, $E_\alpha$ is a characteristic X-ray energy of the element $\alpha$, and $E_\beta$ is a characteristic X-ray energy of the element $\beta$.

The conversion value calculating portion 44 calculates energy conversion values (gain A and offset B) using Eqs. (2) and (3). The conversion value calculating portion 44 obtains the energy values $X_\alpha$ and $X_\beta$ of assigned peaks by selecting two peaks from the constructed X-ray spectrum. The calculating portion 44 acquires the characteristic X-ray energies $E_\alpha$ and $E_\beta$ of the elements $\alpha$ and $\beta$, respectively, from the characteristic X-ray database in the storage portion 54. Preferably, the two peaks selected from the X-ray spectrum are higher than 1 keV and thus are less affected by chemical shifts.

The method of calculating the energy conversion values A and B are not limited to the above-described method. For example, two or more peaks may be selected from the constructed X-ray spectrum, and the energy conversion values A and B may be computed by a least squares method. Additionally, only the gain A may be calculated from one peak of the constructed X-ray spectrum while taking the offset B as a fixed value. Further, only the offset B may be calculated from one peak of the constructed X-ray spectrum while taking the gain A as a fixed value.

The energy calibration decision portion 45 makes a decision as to whether an energy calibration is needed, based on the calculated energy conversion values A and B. For example, the energy calibration decision portion 45 makes a decision as to whether an energy calibration is needed, according to the differences of the calculated energy conversion values A and B with their reference values. For instance, the energy conversion values A and B calculated by the previous energy calibration can be used as the reference values. That is, the energy calibration decision portion 45 makes a decision as to whether an energy calibration is needed, based on the degrees of variation of the energy conversion values A and B.

Specifically, for example, if the differences between the energy conversion values A and B calculated this time and the energy conversion values A and B calculated the previous time are greater than a preset threshold value, the energy calibration decision portion 45 determines that an energy calibration is necessitated. For example, if at least one of the difference between the gain A calculated this time and the gain A calculated the previous time and the difference between the offset B calculated this time and the offset B calculated the previous time is greater than the preset threshold value, the energy calibration decision portion 45 determines that an energy calibration is needed. The threshold value can be set at will.

The notification portion 46 gives a notice as to whether an energy calibration is needed, based on the result of the decision made by the energy calibration decision portion 45. If the energy calibration decision portion 45 has determined that an energy calibration is needed, the notification portion 46 gives a notice to the user to the effect that an energy calibration is needed. The notification is constructed, for example, by displaying a message on the display unit 52, lighting up a warning light (not shown), or sounding a buzzer. No restriction is imposed on the method of notification.

If the energy calibration decision portion 45 has determined that no energy calibration is needed, the notification portion 46 may give a notice to the user to the effect that no energy calibration is needed.

1.2. Operation of Sample Analyzer

Figure 2:
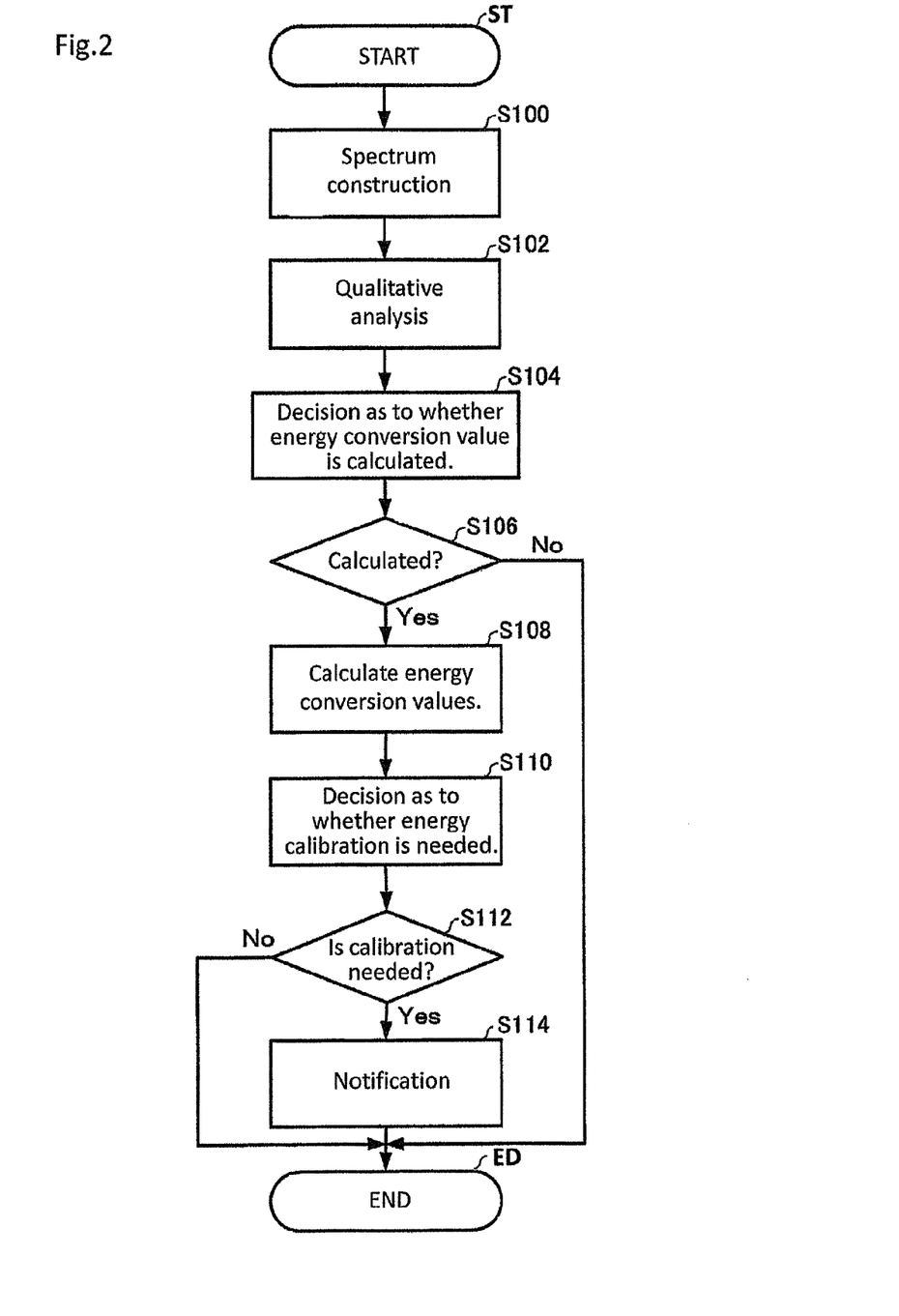
FIG. 2 is a flowchart illustrating one example of subroutine performed by a controller included in a radiation detector assembly shown in FIG. 1.

The operation of the sample analyzer 1 associated with the present embodiment is next described by referring to FIG. 2, which is a flowchart illustrating one example of subroutine performed by the spectrum analysis system 40 of the radiation detector assembly 100 associated with the present embodiment.

In the sample analyzer 1, when the excitation source 2 irradiates the sample S with the primary X-rays Px, the secondary X-rays Sx are produced from the sample S. The detector 10 detects the secondary X-rays Sx and provides an output of staircase waveform having steps whose heights correspond to the energies (wavelengths) of incident X-rays. The pulse processor 20 converts the heights of the steps of the staircase waveform output signal from the detector 10 into pulses whose numbers are proportional to the heights and outputs pulse signals.

The multichannel analyzer 30 digitizes the analog pulse signal delivered from the pulse processor 20, makes the pulse heights of the pulses correspond to the channels of the multichannel analyzer 30, and creates a graph of a distribution of pulse heights from the numbers of pulses counted for the individual channels.

Figure 3:
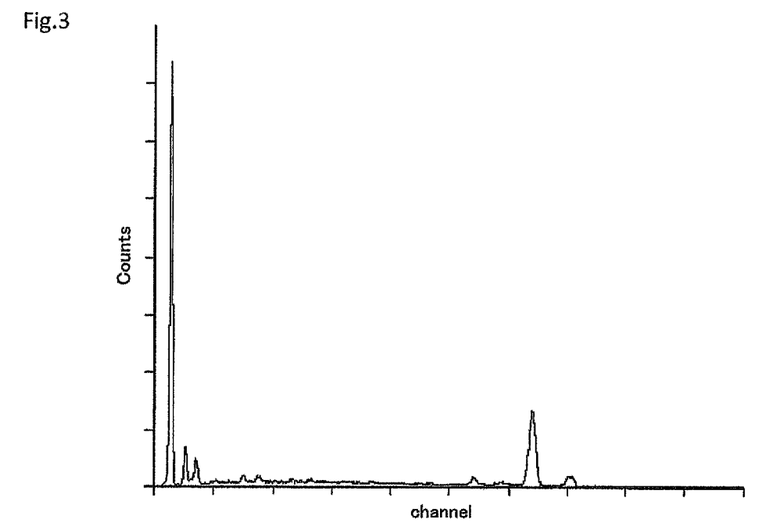
FIG. 3 is a graph showing one example of pulse height distribution created by a multichannel analyzer shown in FIG. 1.

FIG. 3 shows one example of graph of a distribution of pulse heights created by the multichannel analyzer 30. This graph of a distribution of pulse heights is a histogram in which channel (pulse height value) is plotted on the horizontal axis, while the number of counted pulses is plotted on the vertical axis as shown in FIG. 3.

The spectrum constructor 41 constructs an X-ray spectrum from the pulse height distribution graph created by the multichannel analyzer 30, at step S100. In particular, the spectrum constructor 41 constructs an X-ray spectrum by converting the channel (pulse height value) ch on the horizontal axis of the pulse height distribution graph of FIG. 3 into energy E using the energy conversion formula (1). The value $a_b$ of the gain A and the value $b_b$ of the offset value B calculated in the previous energy calibration are used as the values, respectively, of the gain A and offset B. That is, in this example, the energy conversion formula (1) is expressed as follows:

$$E = a_b \times ch + b_b$$

The spectrum constructor 41 constructs an X-ray spectrum by converting the channel (pulse height value) ch on the horizontal axis of the pulse height distribution graph of FIG. 3 using the above formula into the energy E.

Figure 4:
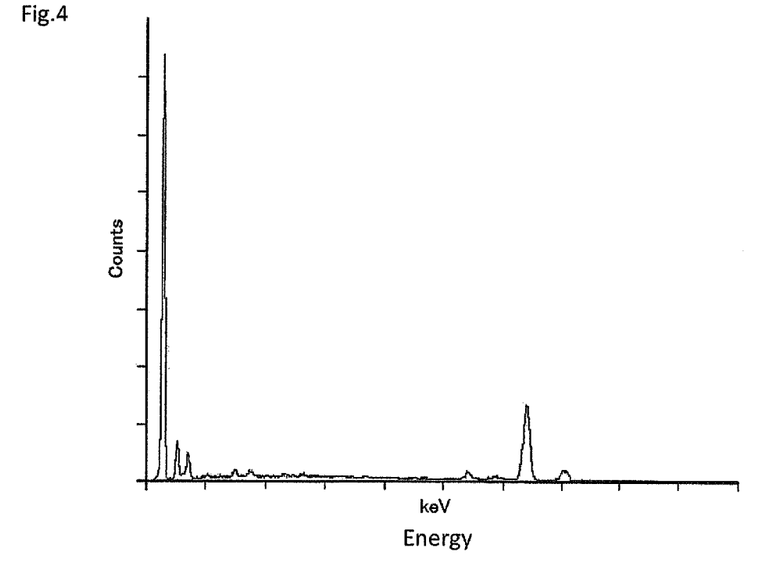
FIG. 4 is a graph showing one example of X-ray spectrum constructed by a spectrum generator included in the radiation detector assembly shown in FIG. 1.

FIG. 4 is one example of X-ray spectrum constructed by the spectrum constructor 41. As shown in FIG. 4, in the X-ray spectrum, the pulse heights on the horizontal axis is converted into X-ray energies.

Then, the qualitative analysis portion 42 assigns the peaks appearing in the X-ray spectrum, at step S102. The qualitative analysis portion 42 performs a qualitative analysis based on the characteristic X-ray database stored in the storage portion 54.

Figure 5:
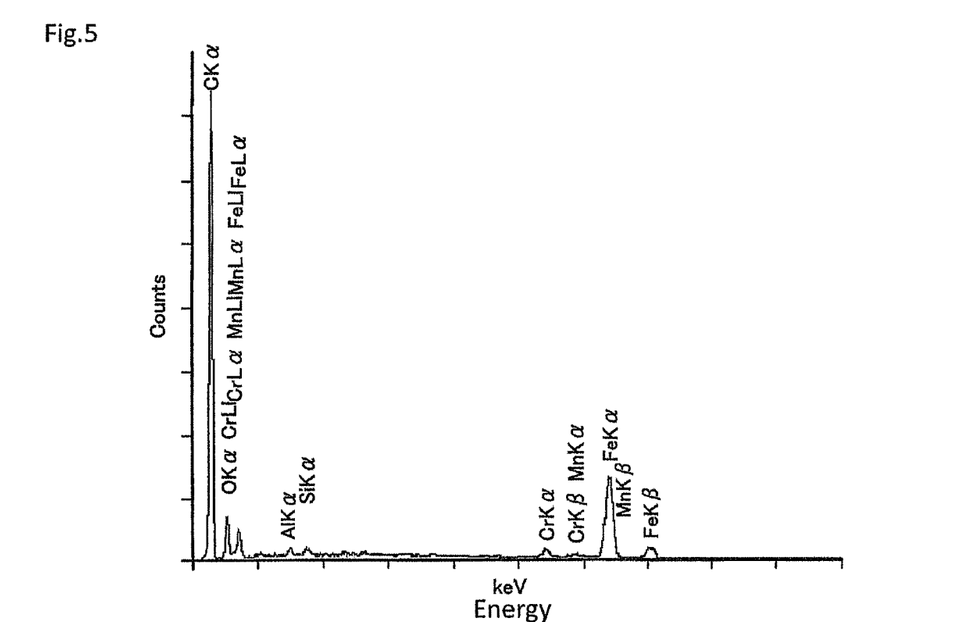
FIG. 5 is a graph showing one example of results of qualitative analysis.

FIG. 5 shows one example of the result of a qualitative analysis. As shown in FIG. 5, the qualitative analysis portion 42 assigns main peaks appearing in the X-ray spectrum to chemical elements.

Then, the conversion value calculation decision portion 43 makes a decision as to whether the energy conversion values should be calculated, based on the assigned peaks, at step S104. If any difference in energy value between the assigned peaks of the X-ray spectrum is 1 keV or higher, the conversion value calculation decision portion 43 determines that the energy conversion values should be calculated. If not so, the decision portion 43 determines that the energy conversion values are not calculated.

If the conversion value calculation decision portion 43 has determined that the energy conversion values should not be calculated (i.e., decision at step S106 is negative (NO)), the processor 40 ends the subroutine. That is, in this case, any decision as to whether an energy calibration is performed is not made.

On the other hand, if the conversion value calculation decision portion 43 determines that the energy conversion values are calculated (i.e., decision at step S106 is affirmative (YES)), the conversion value calculating portion 44 calculates the energy conversion values A and B based on the assigned peaks, at step S108. The conversion value calculating portion 44 selects peaks appropriate for calculation of the energy conversion values A and B from the assigned peaks shown in FIG. 5 and calculates the energy conversion values (gain A and offset B) using Eqs. (2) and (3).

Figure 6:
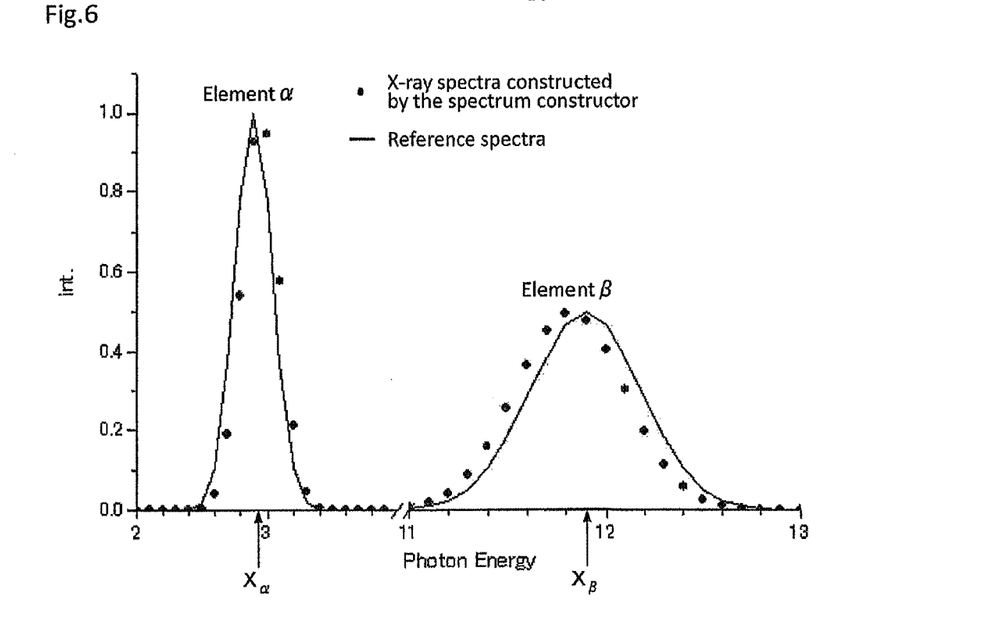
FIG. 6 is a graph illustrating a method of calculating energy conversion values.

FIG. 6 illustrates a method of calculating the energy conversion values A and B. In FIG. 6, X-ray spectra constructed by the spectrum constructor 41 are indicated by dots. Reference spectra for the elements α and β are indicated by solid lines.

Table 1 given below shows energy values $X_\alpha$ and $X_\beta$ of the assigned peaks of the X-ray spectrum shown in FIG. 6 and characteristic X-ray energies $E_\alpha$ and $E_\beta$ of the elements α and β, respectively.

TABLE 1

| element | energy value of peak | characteristic X-ray energy |
|---------|---------------------|----------------------------|
| α       | 2.954               | 3.000                      |
| β       | 11.921              | 12.000                     |

The conversion value calculating portion 44 obtains the energy values $X_\alpha$ and $X_\beta$ of the peaks by selecting two peaks from the constructed X-ray spectrum and obtains the characteristic energies $E_\alpha$ and $E_\beta$ of the elements α and β, respectively, from the characteristic X-ray database stored in the storage portion 54.

The conversion value calculating portion 44 calculates the gain A and the offset B from values listed in Table 1 using Eqs. (2) and (3), respectively, as shown below.

$$A = (E_\beta - E_\alpha)/(X_\beta - X_\alpha) = (12.000 - 3.000)/(11.921 - 2.954) = 1.004$$

$$B = (E_\alpha \times X_\beta - E_\beta \times X_\alpha)/(X_\beta - X_\alpha) = (3.000 \times 11.921 - 12.000 \times 2.954)/(11.921 - 2.954) = 0.035$$

Then, the energy calibration decision portion 45 makes a decision as to whether an energy calibration is needed, based on the energy conversion values A and B calculated by the conversion value calculating portion 44, at step S110. For example, if the difference $|a_a - a_b|$ between the value of the gain A ($A = a_a = 1.004$) calculated this time and the value of the gain A calculated the previous time ($A = a_b$) is greater than a preset threshold value for the gain, or if the difference $|b_a - b_b|$ between the value of the offset B calculated this time ($B = b_a = 0.035$) and the value of the offset B calculated the previous time ($B = b_b$) is greater than a preset threshold value for the offset, the energy calibration decision portion 45 determines that an energy calibration is needed.

That is, if at least one of the differences $|a_a - a_b|$ and $|b_a\ b_b|$ is greater than its threshold value, the energy calibration decision portion 45 determines that an energy calibration is needed.

If the difference $|a_a - a_b|$ between the values of the gain S is equal to or less than the threshold value for the gain and, at the same time, the difference $|b_a - b_b|$ between the values of the offset B is equal to or less than the threshold value for the offset, the energy calibration decision portion 45 determines that no energy calibration is needed.

If the energy calibration decision portion 45 determines that an energy calibration is needed (i.e., decision at step S112 is YES), the notification portion 46 displays a message on the display unit 52 to the effect that an energy calibration is needed and gives a notice to the user (step S114). The spectrum analysis system 40 ends the subroutine.

On the other hand, if the energy calibration decision portion 45 has determined that no energy calibration is needed (decision at step S112 is NO), the spectrum analysis system 40 ends the subroutine. At this time, the notification portion 46 may display a message on the display unit 52 to the effect that no energy calibration is needed.

The radiation detector assembly 100 and sample analyzer 1 associated with the present embodiment have the following features.

The radiation detector assembly 100 is configured including the qualitative analysis portion 42 for assigning the peaks appearing in the X-ray spectrum, the conversion value calculating portion 44 for calculating the energy conversion values A and B used to convert the pulse heights of pulses into X-ray energies based on the assigned peaks, and the energy calibration decision portion 45 for making a decision as to whether an energy calibration is needed based on the calculated energy conversion values A and B. Therefore, the radiation detector assembly 100 can calculate the energy conversion values based on peaks assigned by a qualitative analysis and make a decision as to whether an energy calibration is needed. Consequently, if any measurement on a reference sample for energy calibration is not made, it is possible to make a decision as to whether an energy calibration is needed from the results of a measurement on a sample containing unknown elements. Hence, it is easy to make a decision as to whether an energy calibration is needed.

Accordingly, the radiation detector assembly 100 makes it possible to make a decision as to whether an energy calibration is needed during normal measurements on samples to be investigated. As a consequence, it is possible to prevent an energy calibration from being performed, for example, in spite of the fact that no energy calibration is necessary. Furthermore, it is possible to prevent the resulting energy position deviation from exceeding the tolerable range during continuous measurement on plural samples.

The radiation detector assembly 100 includes the notification portion 46 that gives a notice as to whether an energy calibration is needed based on the result of decision made by the energy calibration decision portion 45 and, therefore, the user can appropriately judge whether an energy calibration is necessary.

The radiation detector assembly 100 includes the conversion value calculation decision portion 43 for making a decision as to whether the energy conversion values A and B are calculated, based on the assigned peaks. If the conversion value calculation decision portion 43 has determined that the energy conversion values A and B are not calculated, the conversion value calculating portion 44 does not perform calculation of the energy conversion values A and B. Consequently, it is possible to prevent the energy conversion values A and B from being calculated inaccurately.

Since the sample analyzer 1 includes the radiation detector assembly associated with the present invention, it is easy to make a decision as to whether an energy calibration is needed as described previously.

Modifications

Modifications of the radiation detector assembly and sample analyzer associated with the present embodiment are next described. Those components of radiation detector assembly and sample analyzer associated with the modifications described below which are similar in function with their respective counterparts of the radiation detector assembly 100 and the sample analyzer 1 associated with the present embodiment are indicated by the same reference numerals as in the above-cited figures and that a detailed description thereof is omitted.

(1) First Modification

Figure 7:
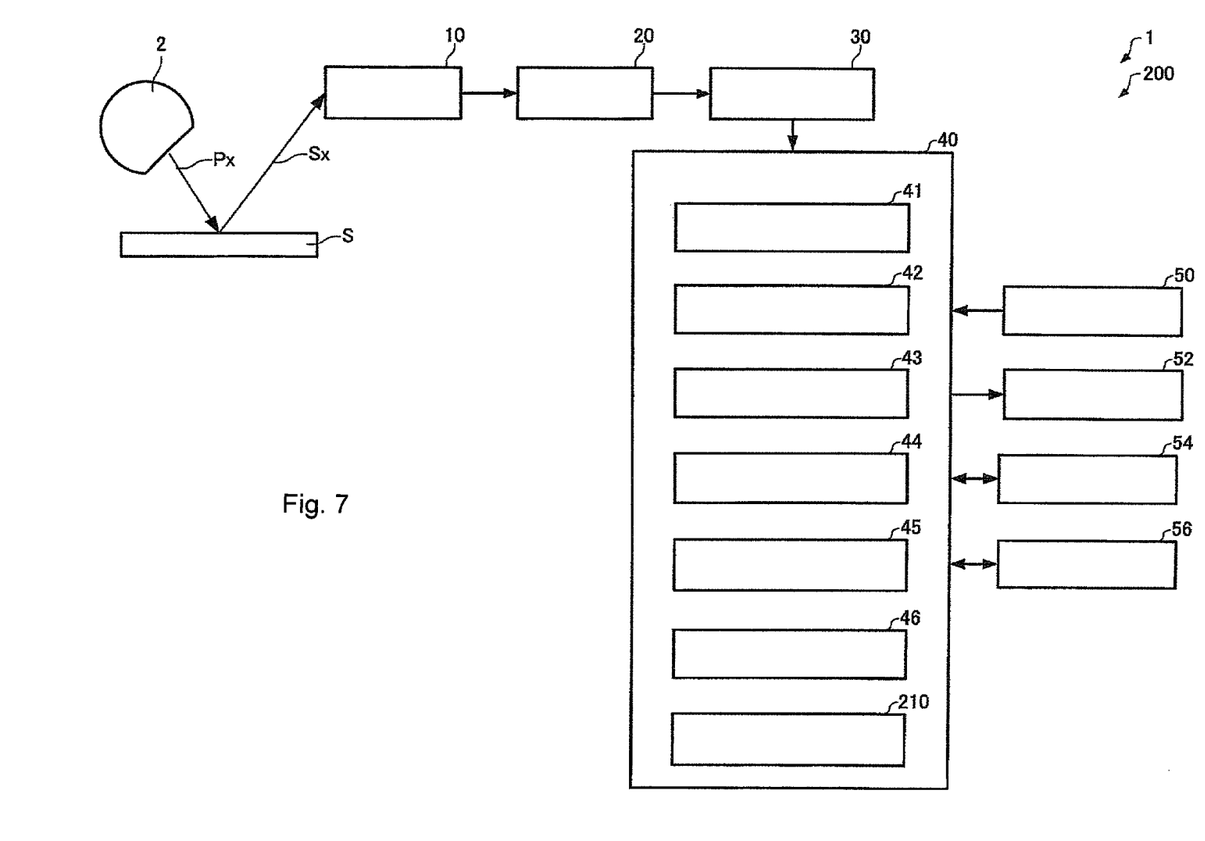
FIG. 7 is a block diagram of a radiation detector assembly associated with a first modification of the above-described embodiment, showing the configuration of the assembly.

A first modification is first described. FIG. 7 shows the configuration of a radiation detector assembly, 200, associated with the first modification.

As shown in FIG. 7, the radiation detector assembly 200 is configured including an energy calibration portion 210.

If the energy calibration decision portion 45 has determined that an energy calibration is needed, the energy calibration portion 210 performs an energy calibration using the energy conversion values A and B calculated by the conversion value calculating portion 44. In particular, the energy calibration portion 210 varies the energy conversion values A and B of energy conversion formula (1) to the energy conversion values A and B calculated by the current energy calibration.

Figure 8:
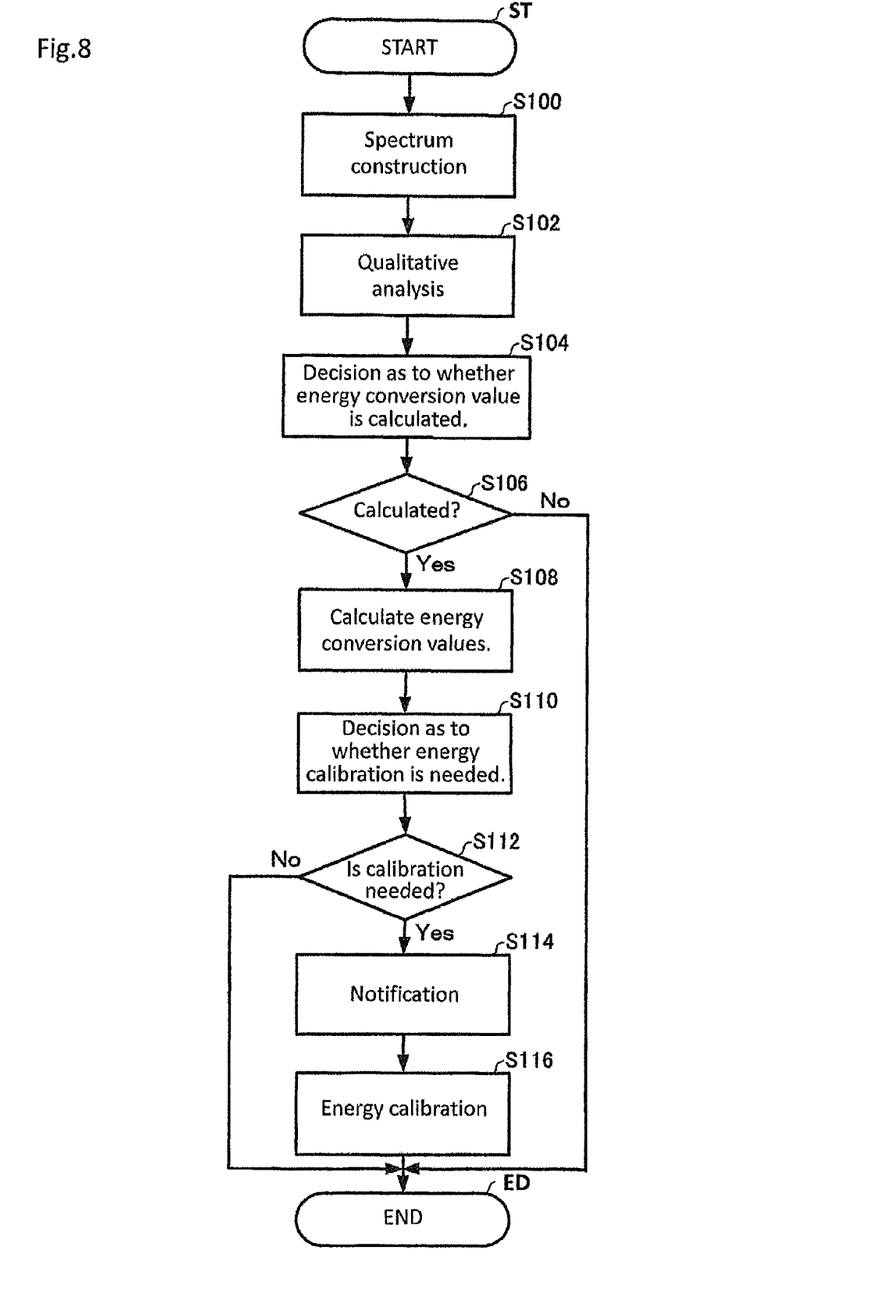
FIG. 8 is a flowchart showing one example of subroutine performed by a processor included in the radiation detector assembly shown in FIG. 7.

The operation of the radiation detector assembly 200 is next described. FIG. 8 is a flowchart illustrating one example of subroutine performed by a spectrum analysis system 40 included in the radiation detector assembly 200. Those steps of the flowchart of FIG. 8 which are identical with their respective counterparts of the flowchart of FIG. 2 are indicated by the same reference numerals as in FIG. 2 and a description thereof is omitted.

As illustrated in FIG. 8, if the energy calibration decision portion 45 has determined that an energy calibration is needed (i.e., decision at step S112 is YES), the notification portion 46 displays a message on the display unit 52 to the effect that an energy calibration is needed, at step S114.

Then, the energy calibration portion 210 performs an energy calibration using the value $a_a=1.004$ of the gain A and the value $B_a=0.035$ of the offset B calculated by the conversion value calculating portion 44, at step S116. In particular, the energy calibration portion 210 uses the value $a_a=1.004$ of the gain and the value $b_a=0.035$ of the offset calculated this time instead of the value $a_b$ of the gain A and the value $b_a$ of the offset B calculated the previous time and modifies the energy conversion formula (1) as follows:

$$E=a_a \times ch + b_a = 1.004 \times ch + 0.035$$

As a result, an energy calibration can be performed. The spectrum analysis system 40 ends the subroutine.

The radiation detector assembly 200 may perform the step S116 of performing an energy calibration without performing the step S114 for giving a notice. In this case, the notification portion 46 may display a message on the display unit 52 to the effect that an energy calibration has been done after the execution of the step S116 for performing an energy calibration.

If the energy calibration decision portion 45 has determined that an energy calibration is needed, the radiation detector assembly 200 can perform an energy calibration using the energy conversion values A and B calculated by the conversion value calculating portion 44. Therefore, the radiation detector assembly 200 permits automation of energy calibration.

(2) Second Modification

A second modification is next described.

In the above-described radiation detector assembly 100, the conversion value calculating portion 44 calculates the energy conversion values A and B using Eqs. (2) and (3). Alternatively, the conversion value calculating portion 44 may compute the energy conversion values A and B based on a reference spectrum of an element corresponding to the assigned peaks.

Specifically, the conversion value calculating portion 44 first performs spectral fitting (regression analysis) using a reference spectrum of an element corresponding to the assigned peaks, and finds a value determining the degree of fitting of a residual error, a determination coefficient, or the like. Then, the energy conversion values are varied to improve the degree of fitting such that they fall within desired ranges. That is, a step of computationally converting the energy conversion values A and B is performed. Consequently, the energy conversion values A and B can be calculated.

In the description provided thus far, the conversion value calculating portion 44 performs spectral fitting using a reference spectrum. Alternatively, spectral fitting may be performed using a base function showing a spectral shape such as a gaussian function.

Figure 9:
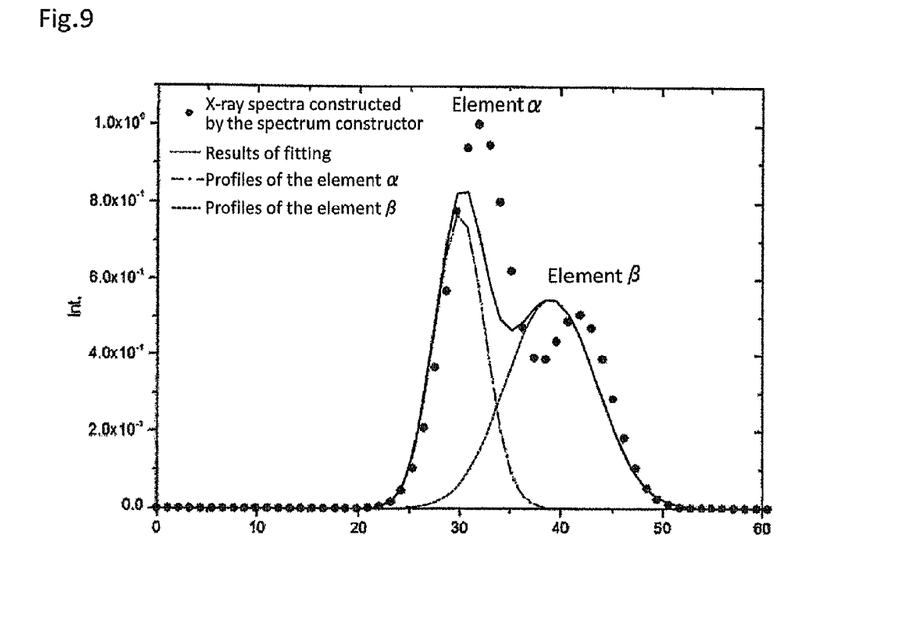
FIG. 9 is a graph illustrating a method of calculating energy conversion values in accordance with a second modification of the above-described embodiment.
Figure 10:
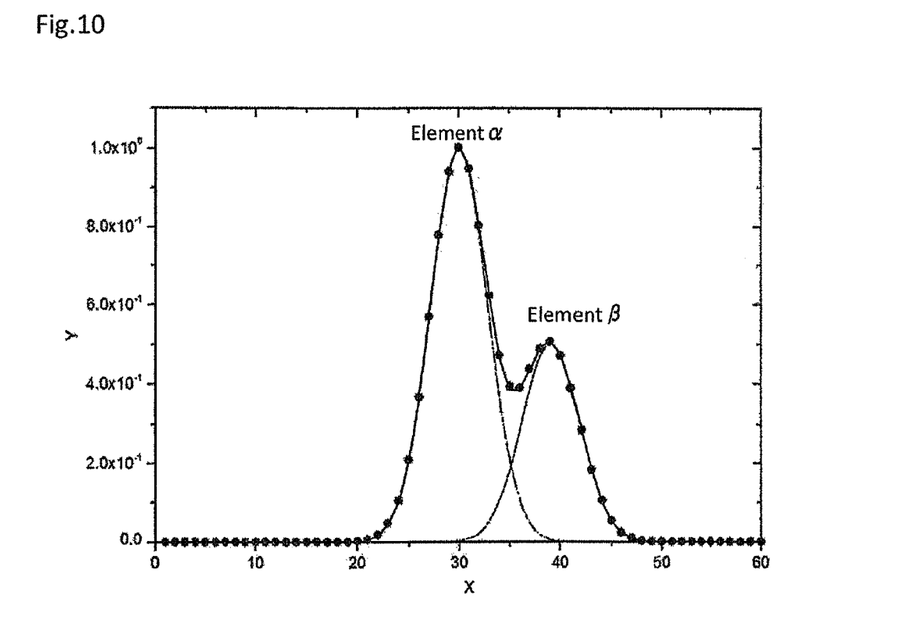
FIG. 10 is a graph illustrating another method of calculating energy conversion values in accordance with the second modification.

Then, step S108 (associated with the present modification) performed by the conversion value calculating portion 44 to calculate the energy conversion values is next described by referring to FIGS. 9 and 10, which illustrate a method of calculating the energy conversion values A and B in accordance with the present modification. In FIGS. 9 and 10, X-ray spectra constructed by the spectrum constructor 41 are indicated by dots. The results of fitting are indicated by solid lines. Profiles of the element α are indicated by dot-and-dash lines. Profiles of the element β are indicated by dotted lines.

As shown in FIG. 9, the conversion value calculating portion 44 performs spectral fitting using either the reference spectrum of the element α assigned by the qualitative analysis portion 42 and the reference spectrum of the element β or a base function, obtains profiles of the elements α and β, and obtains a value determining the degree of fitting such as a residual error, a determination coefficient, or the like. In the example of FIG. 9, the determination coefficient is 0.96.

The conversion value calculating value 44 varies the values of the gain A and offset B such that the degree of fitting falls within a desired range as shown in FIG. 10 and is improved. In the example of FIG. 10, the determination coefficient is 1.0. Thus, the values of the gain A and offset B are computationally converged. In this way, the conversion value calculating portion 44 can calculate the energy conversion values (i.e., the gain A and offset B).

According to the present modification, if peaks for calculating the energy conversion values A and B are close to each other or overlap with each other, the energy conversion values A and B can be calculated accurately.

(3) Third Modification

Figure 11:
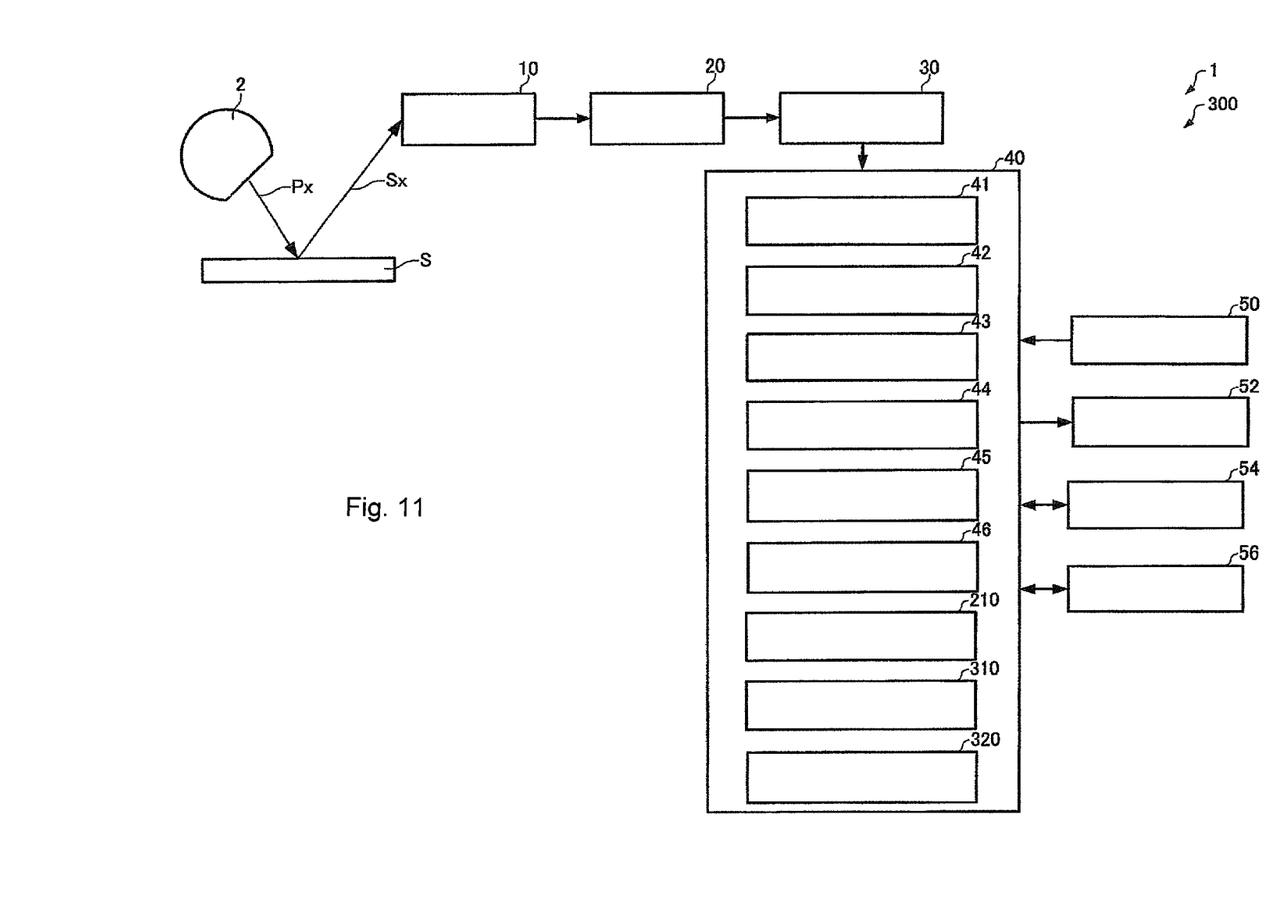
FIG. 11 is a block diagram of a radiation detector assembly associated with a third modification of the above-described embodiment.

A third modification is next described. FIG. 11 shows the configuration of a radiation detector assembly, 300, associated with the third embodiment.

In the above-described radiation detector assembly 100, the conversion value calculating portion 44 calculates the energy conversion values based on the peaks assigned by a qualitative analysis, and the energy calibration decision portion 45 makes a decision as to whether an energy calibration is needed. Consequently, the radiation detector assembly 100 can easily make a decision as to whether an energy calibration is needed.

In contrast, the radiation detector assembly 300, as shown in FIG. 11, is configured including a resolution calculating portion 310 and a resolution calibration decision portion 320. The resolution calculating portion 310 calculates an energy resolution calibration value that is a dispersion $\sigma_0$ associated with system noise, based on the energy values of the assigned peaks. The resolution calibration decision portion 320 makes a decision based on the calculated energy resolution calibration value (dispersion $\sigma_0$) as to whether an energy calibration is needed. Consequently, the radiation calibration decision portion 320 can easily make a decision as to whether energy resolution needs to be calibrated.

In the radiation detector assembly using an energy-dispersive detector, the energy resolution may vary as well as the energy position due to aging variations of the detector 10 and signal processing circuitry located behind the detector and including the pulse processor 20 and multichannel analyzer 30. If the energy resolution varies, peak intensities may not be found accurately during spectral analysis when quantitative computation is being performed by the radiation detector assembly and so accurate qualitative results may not be obtained.

Figure 12:
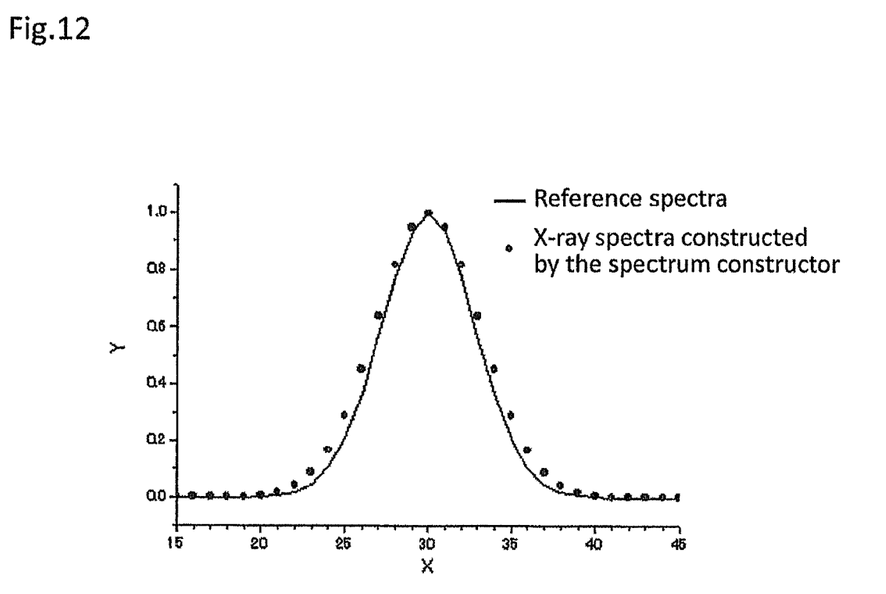
FIG. 12 is a graph illustrating energy resolution.

FIG. 12 illustrates energy resolution. In FIG. 12, a reference spectrum is indicated by solid lines. An X-ray spectrum constructed by the spectrum constructor 41 is indicated by dotted lines.

As shown in FIG. 12, if the peak width of an X-ray spectrum is different from the peak width of a reference spectrum, the value indicative of the degree of fitting such as a determination coefficient or residual error deteriorates. Energy resolution can be calibrated by varying the peak width of the reference spectrum so as to improve the degree of fitting to peaks of the X-ray spectrum. Calibration of energy resolution referred to herein is to find the dispersion $\sigma_0$ of the following Eq. (4) that determines the peak width of the reference spectrum.

$$\sigma^2 = ConstA \cdot E + \sigma_0^2 \qquad (4)$$

where E is an energy, $\sigma$ is the resolution at the energy E, $\sigma_0$ is a dispersion associated with system noise, and ConstA is a constant depending on the type of the detector. Reference spectra for various elements are registered, for example, in the characteristic X-ray database stored in the storage portion 54. The peak width of the reference spectra of the elements registered in the characteristic X-ray database is determined by the above Eq. (4).

After the energy conversion values A and B are calculated by the conversion value calculating portion 44, the resolution calculating portion 310 varies the peak width (dispersion $\sigma_0$) of the reference spectra, performs spectral fitting to the X-ray spectra converted using the energy conversion values A and B, and computationally converges the value of the peak width (dispersion $\sigma_0$) to improve the value determining the degree of fitting such as a residual error or a determination coefficient such that the value falls within a desired range. Consequently, the value of the dispersion $\sigma_0$ can be calculated.

The resolution calibration decision portion 320 makes a decision as to whether an energy calibration is needed, based on the peak width (dispersion $\sigma_0$) calculated by the resolution calculating portion 310. For example, the resolution calibration decision portion 320 makes a decision as to whether an energy calibration is needed, based on the difference between the calculated peak width (dispersion $\sigma_0$) and a reference value. For example, the peak width (dispersion $\sigma_0$) calculated by the previous calibration of energy resolution can be used as the reference value.

Specifically, if the difference between the peak value (dispersion $\sigma_0$) calculated this time and the peak value (dispersion $\sigma_0$) calculated the previous time is greater than a preset threshold value, the resolution calibration decision portion 320 determines that energy resolution needs to be calibrated. The threshold value can be set at will.

In this case, the peak width of a reference spectrum is found in calibrating energy resolution. Alternatively, energy resolution may be calibrated by finding the peak width of a base function showing a spectral shape such as a gaussian function.

Figure 13:
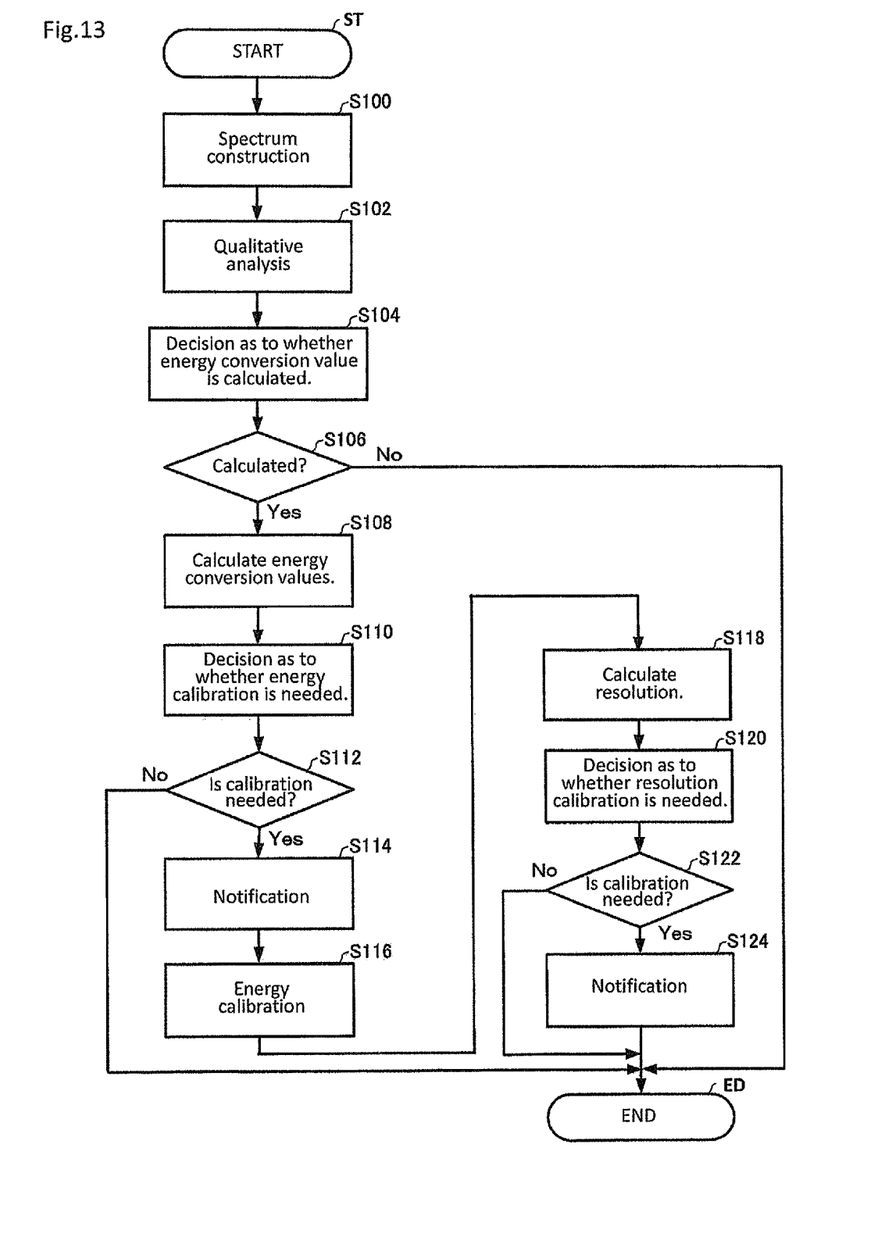
FIG. 13 is a flowchart illustrating one example of subroutine performed by the radiation detector assembly shown in FIG. 11.

The operation of the radiation detector assembly 300 is next described by referring to the flowchart of FIG. 13, which illustrates one example of subroutine performed by the spectrum analysis system 40 of the radiation detector assembly 300. Those processing steps of the flowchart of FIG. 13 which are identical with their respective counterparts of the flowchart of FIGS. 2 and 8 are indicated by the same reference numerals as in FIGS. 2 and 8 and a description thereof is omitted.

As illustrated in FIG. 13, if the energy calibration decision portion 45 has determined that an energy calibration is needed (i.e., the decision at step S112 is YES), the notification portion 46 displays a message on the display unit 52 to the effect that an energy calibration is needed, at step S114.

Then, the energy calibration portion 210 performs an energy calibration, using the value $a_a$=1.004 of the gain A and the value $b_a$=0.035 of the offset B calculated by the conversion value calculating portion 44, at step S116. In particular, the energy calibration portion 210 rewrites the energy conversion formula (1) as follows, using the value $a_a$=1.004 of the gain A and the value $b_a$=0.035 of the offset B calculated this time instead of the value $a_b$ of the gain A and the value $b_b$ of the offset B calculated the previous time.

$$E = a_a \times ch + b_a = 1.004 \times ch + 0.035 \qquad (5)$$

As a consequence, an energy calibration can be performed.

Then, the resolution calculating portion 310 again creates an X-ray spectrum using Eq. (5) above, varies the peak width ($\sigma_0$) of the reference spectrum of the element $\alpha$ and the reference spectrum of the element $\beta$ or a base function, performs spectral fitting to this X-ray spectrum, and computationally converges the peak width (dispersion $\sigma_0$) such that the degree of fitting such as a residual error or a determination coefficient falls within a desired range, at step S118.

Then, the resolution calibration decision portion 320 makes a decision as to whether an energy calibration is needed, based on the peak width (dispersion $\sigma_0$) calculated by the resolution calculating portion 310, at step S120.

If the difference $|\sigma_0(a)-\sigma_0(b)|$ between the value (dispersion $\sigma_0=\sigma_0(a)$) of the peak width calculated this time and the value (dispersion $\sigma_0=\sigma_0(b)$) of the peak width calculated the previous time is greater than a preset threshold value for the peak value (dispersion $\sigma_0$), the resolution calibration decision portion 320 determines that energy resolution needs to be calibrated. If the difference $|\sigma_0(a)-\sigma_0(b)|$ is equal to or less than the preset threshold value for the peak width (dispersion $\sigma_0$), the resolution calibration decision portion 320 determines that energy resolution needs to be calibrated.

If the resolution calibration decision portion 320 has determined that energy resolution needs to be calibrated (i.e., decision at step S122 is YES), the notification portion 46 displays a message on the display unit 52 to the effect that energy resolution needs to be calibrated and gives a notice to the user. Then, the spectrum analysis system 40 ends the subroutine.

On the other hand, if the resolution calibration decision portion 320 has determined that energy resolution needs to be calibrated (i.e., the decision at step S122 is NO), the spectrum analysis system 40 ends the subroutine.

The radiation detector assembly 300 may be configured including a resolution calibration portion (not shown) which, if the resolution calibration decision portion 320 has determined that an energy calibration is needed, calibrates energy resolution using the peak value (dispersion $\sigma_0$) of the peak width calculated by the resolution calculating portion 310. In particular, the resolution calibration portion varies the value of $\sigma_0$ in Eq. (4) determining the peak width of the reference spectrum of characteristic X-rays to the calculated value of the dispersion $\sigma_0$.

The radiation detector assembly 300 can easily make a decision as to whether an energy resolution needs to be calibrated, in addition to a decision as to whether an energy calibration is needed. Consequently, it is possible to prevent execution of calibration of energy resolution, for example, in spite of the fact that energy resolution does not need to be calibrated.

It is to be noted that the above-described embodiment is only exemplary and that the invention is not restricted thereto.

The above-described radiation detector assemblies 100, 200, and 300 are fluorescence X-ray analyzers which detect fluorescence X-rays Sx and construct X-ray spectra. The radiation detector assembly associated with the present invention may also be an instrument which detects other radiation (such as gamma rays) and constructs a radiation spectrum (such as a gamma-ray spectrum).

The excitation source 2 (see FIGS. 1, 7, and 11) of the above-described sample analyzer 1 irradiates the sample S with X-rays Px. Alternatively, the excitation source 2 may irradiate the sample S with an electron beam, ions, or gamma rays to produce the X-rays Sx from the sample S. That is, the sample analyzer associated with the present invention is not restricted to an fluorescence X-ray analyzer. The sample analyzer may also be an electron probe microanalyzer or an electron microscope (such as a transmission electron microscope (TEM), a scanning transmission electron microscope (STEM), or a scanning electron microscope) equipped with a radiation detector assembly associated with the present invention.

The present invention embraces configurations (e.g., configurations identical in function, method, and results or identical in purpose and advantageous effects) which are substantially identical to the configurations described in the above embodiment. Furthermore, the invention embraces configurations which are similar to the configurations described in the above embodiment except that their nonessential portions have been replaced. Additionally, the invention embraces configurations which are identical in advantageous effects to, or which can achieve the same object as, the configurations described in the above embodiment. Further, the invention embraces configurations which are similar to the configurations described in the above embodiment except that a well-known technique is added.

What is claimed is:

1. A radiation detector assembly for detecting radiations, producing pulse signals having pulse heights corresponding to energies of the radiations, converting the pulse heights of the pulse signals into radiation energies, and creating a radiation spectrum, said radiation detector assembly comprising:
   a qualitative analysis portion for assigning peaks appearing in the radiation spectrum;
   a conversion value calculating portion for calculating energy conversion values used to convert the pulse heights into the radiation energies based on the assigned peaks; and
   an energy calibration decision portion for making a decision, based on the calculated energy conversion values, as to whether an energy calibration is needed.

2. The radiation detector assembly as set forth in claim 1, further comprising a notification portion which gives a notice as to whether an energy calibration is needed, based on the result of the decision made by said energy calibration decision portion.

3. The radiation detector assembly as set forth in claim 1, further comprising an energy calibration portion which, if said energy calibration decision portion has determined that an energy calibration is needed, performs an energy calibration using said energy conversion values calculated by said conversion value calculating portion.

4. The radiation detector assembly as set forth in claim 1, wherein there is further provided a conversion value calculation decision portion for making a decision as to whether said energy conversion values should be calculated, based on the assigned peaks, and wherein, if the conversion value calculating portion has determined that the energy conversion values are not calculated, the conversion value calculating portion does not perform calculation of the energy conversion values.

5. The radiation detector assembly as set forth in claim 1, wherein said conversion value calculating portion calculates said energy conversion values, based either on a reference spectrum of an element corresponding to the assigned peaks or on a base function.

6. The radiation detector assembly as set forth in claim 1, further comprising:
   a resolution calculating portion for calculating an energy resolution calibration value, based on the assigned peaks, to convert said pulse heights into said radiation energies; and
   a resolution calibration decision portion for making a decision as to whether energy resolution needs to be calibrated, based on the calculated energy resolution calibration value.

7. A sample analyzer including a radiation detector assembly as set forth in claim 1.

* * * * *